United States Patent [19]

Wenke et al.

[11] Patent Number: 5,792,220
[45] Date of Patent: Aug. 11, 1998

[54] DYEING HAIR WITH MELANIN PROCURSORS IN THE PRESENCE OF IODATE AND PEROXIDE

[75] Inventors: Gottfried Wenke, Woodbridge, Conn.; Giuseppe Prota, Naples, Italy

[73] Assignee: Bristol-Myers Squibb Company, New York, N.Y.

[21] Appl. No.: 857,632

[22] Filed: May 16, 1997

[51] Int. Cl.$^6$ ............................................. A61K 7/13
[52] U.S. Cl. .................. 8/409; 8/406; 8/408; 8/423; 8/432
[58] Field of Search ....................... 8/406, 408, 409, 8/423, 421, 132

[56] References Cited

U.S. PATENT DOCUMENTS

| | | | |
|---|---|---|---|
| 2,934,396 | 4/1960 | Charle et al. | 8/423 |
| 3,194,734 | 7/1965 | Seemuller et al. | 8/423 |
| 3,993,436 | 11/1976 | Fujinuma | 8/424 |
| 4,746,322 | 5/1988 | Herlihy | 8/405 |
| 4,804,385 | 2/1989 | Grollier et al. | 8/423 |
| 4,904,274 | 2/1990 | Schultz et al. | 8/406 |
| 5,006,127 | 4/1991 | Tennigkeit et al. | 8/406 |
| 5,131,911 | 7/1992 | Lang et al. | 8/408 |
| 5,173,085 | 12/1992 | Brown et al. | 8/405 |
| 5,178,637 | 1/1993 | Lagrange et al. | 8/423 |

FOREIGN PATENT DOCUMENTS

| | | | |
|---|---|---|---|
| 3628397 A1 | 2/1988 | Germany | A61K 7/13 |

*Primary Examiner*—Paul Lieberman
*Assistant Examiner*—Caroline L. Dusheck
*Attorney, Agent, or Firm*—Charles J. Zeller

[57] ABSTRACT

The present invention concerns improved processes for dyeing keratinous fibers especially hair on the human scalp using a two-step oxidation process for the oxidation of the melanin precursors 5,6-dihydroxyindoline (DHIN), 5,6-dihydroxyindole (DHI), and derivatives thereof such as 5,6-dihydroxyindole-2-carboxylic acid (DHICA).

16 Claims, No Drawings

DYEING HAIR WITH MELANIN PROCURSORS IN THE PRESENCE OF IODATE AND PEROXIDE

FIELD OF THE INVENTION

The present invention concerns improved processes for dyeing keratinous fibers especially hair on the human scalp using a two-step oxidation process for the oxidation of the melanin precursors 5,6-dihydroxyindoline (DHIN), 5,6-dihydroxyindole (DHI), and derivatives thereof such as 5,6-dihydroxyindole-2-carboxylic acid (DHICA).

BACKGROUND OF THE INVENTION

One known method for dyeing hair is based upon the synthesis of melanin and melanin-like materials from melanin precursors. Melanin is a polymer produced from tyrosine by a series of metabolic reactions, but it has become the practice of the art to use DHI or its derivatives as intermediates or precursors in the chemical synthesis of melanin or melanin-like materials.

A number of problems are associated with the use of DHI, however. DHI is difficult and expensive to synthesize and its solutions are unstable in air, oxidizing rapidly to form unwanted by-products that are ineffective as hair colorants. Notwithstanding the reactivity of DHI to oxidation, it is useful to employ an oxidant to convert DHI to melanin during the hair dyeing process. Known oxidants employed for the oxidative polymerization of DHI are, for example, hydrogen peroxide, sodium chlorite, sodium iodide together with hydrogen peroxide, and treatment with a salt of a transition metal cation such as copper sulfate as a catalyst for air oxidation.

A deficiency of the known hair dyeing processes is that the oxidants commonly employed in hair dyeing with melanin precursors do not color virgin hair with intensity and darkness. This deficiency is especially apparent in efforts to achieve hair which is intensely black. Another deficiency is that the known hair dyeing processes, although providing a dark color, form melanin only on the outermost surface of the hair shaft with the result that wearing properties such as light or shampoo fastness are unsatisfactory.

The art has long sought a suitable oxidizing agent for use with DHI and its derivatives which can be employed without the problems discussed above. More specifically, the art has sought dye compositions which will produce melanin in the hair fiber and give the hair a desirable color with lasting wear qualities. Advantageously, the hair is smooth and easy to comb when the melanin is within the hair fiber. In contrast, melanin on the surface of the hair renders hair rough to the touch and difficult to comb.

PRIOR ART

German Offenlegungsschrift DE 3628397A1 relates to a method of dyeing hair by oxidation of oxidative dyes under acid conditions with alkali metal or alkaline earth metal salts such as potassium iodide or dichromate.

U.S. Pat. No. 4,804,385 describes the application of DHI and iodide ions at acid pH followed by treatment with hydrogen peroxide. In this procedure, the final color is determined by the concentration of iodide ion and hydrogen peroxide.

U.S. Pat. No. 5, 173,085 describes a process for dyeing hair with DHI in which the hair is treated with a transition metal salt such as cupric sulfate prior to DHI application. The transition metal ion is believed to catalyze the air oxidation of DHI. The process dyes hair an intense black color that may be lightened by a post-treatment with hydrogen peroxide. Except for air no external oxidizer is employed during the dyeing process.

U.S. Pat. No. 3,194,734 teaches the use of a variety of oxidizing agents with DHI or with 1-, 2- or 3-methyl substituted DHI derivatives in alkaline media in a one or two-step process to color hair. There is no mention of a combination of hydrogen peroxide with selected iodates.

U.S. Pat. No. 4,746,322 describes the dyeing of hair with a composition comprising an organic dye, a melanin precursor such as D-, L- or DL-dopa together with an iodate or periodate salt. There is no mention of the use of a combination of hydrogen peroxide and selected iodate salts.

U.S. Pat. No. 2,934,396 describes a two step process for dyeing hair using DHI in acid solution followed by treatment with either hydrogen peroxide or a bromate, iodate, periodate or persulfate salt as an oxidizing agent.

BRIEF SUMMARY OF THE INVENTION

It has now been found that the drawbacks of the prior art processes can be avoided by oxidatively dyeing human hair in an acidic environment with compositions comprising (a) a melanin precursor such as 5,6-dihydroxyindoline (DHIN), 5,6-dihydroxyindole (DHI), and their derivatives (including analogs and homologs), and (b) an oxidizer component comprising (i) an alkali metal, alkaline earth metal or ammonium iodate in association with (ii) a suitable peroxide, especially hydrogen peroxide. The present invention further includes a process wherein the hair is dyed in a two-step process in which an aqueous solution of the melanin precursor is first applied to hair followed by the subsequent application of the oxidizer component. Optionally, the hair may be treated with a reducing agent prior to or during the application of the aqueous melanin precursor composition. The processes may also be employed utilizing these compositions in conjunction with other known oxidative dyes and mixtures thereof. The invention further includes kits containing such compositions.

DETAILED DESCRIPTION OF THE INVENTION

The process of this invention contemplates two or more sequential steps to achieve the dyeing of the consumer's hair, and is carried out with a kit that contains the two or more sequentially applied compositions used in the process.

In the first step of the process, following optional pre-treatments such as rinsing, shampooing or gentle reduction of the hair with a reducing agent such as thioglycolic acid or other known reducing agent, the hair is contacted with a first aqueous composition (the hair dye lotion) having a pH of from about 3 to 10 and containing the melanin precursor. With rinsing optional, the hair is then contacted with an oxidizer component that comprises an iodate salt (as hereinafter described) and hydrogen peroxide, the pH of the acidic oxidizer component being from about 2 to 10, preferably in the range of 2 to 6.5. In order to achieve the hair dyeing results of the present invention, it is essential to apply the hair dye lotion in advance of the application of the oxidizer component. It is also essential that the oxidation of the melanin precursor on the hair following the application of the oxidizer component takes place at an acidic pH.

The hair dye lotion is typically applied to hair for 5 to 60, preferably 10 to 30 minutes, and may comprise the melanin precursor alone or the precursor in combination with one or more conventional oxidative hair dye primary intermediates and/or couplers. In an alternate embodiment the one or more oxidative hair dye primary intermediates and/or couplers may be contained in a second hair dye lotion composition, which may be applied to the hair before or after application of the melanin precursor-containing hair dye lotion. In a variation of this embodiment a portion of the nonmelaninic oxidative hair dye ingredients may be contained in said second hair dye lotion with the remainder contained in the precursor-containing hair dye lotion or in the oxidizer component as hereinafter described, or a portion of the nonmelaninic oxidative hair dye ingredients may be contained in the precursor-containing hair dye lotion with the remainder contained in the oxidizer component as hereinafter described.

In the preferred embodiment, the selected iodate and peroxide oxidizer component ingredients are contained in one composition that is the oxidizer component. The oxidizer component is applied to the hair for sufficient time to effect substantial oxidation of the melanin precursor and other dye components. Usually, this is for a time period of about 1 to 30 minutes, preferably 5 to 15 minutes, depending on the concentrations of the peroxide and iodate ingredients. In a variation from the preferred method the iodate and the peroxide ingredients are each provided as separate aqueous compositions which together comprise the oxidizer component, and which are intended for sequential application to the hair following application of the melanin precursor-containing hair dye lotion. In such instance the compositions as combined, i.e., as applied to the hair, produce an acidic pH, although preferably each composition is acidic as it is applied to the hair.

In another embodiment the nonmelaninic oxidative hair dye ingredients may be added to the aqueous iodate composition, to the aqueous peroxide composition or to the mixed iodate-peroxide composition, as the case may be, just prior to application to the hair. In such event the kit contains a hair dye lotion containing the DHI, an oxidizer component that may be a single composition or a composition contained in two containers, and a composition of the nonmelaninic oxidative hair dye ingredients, which may be in powder or solution form. Each of the compositions may be provided in a separate container, and is preferably premeasured, each kit preferably being suitable for a single use.

The acidic environment in which the oxidation of the melanin precursor takes place can be obtained in a variety of ways. Preferably, the oxidizer component has a sufficiently acidic pH so that the oxidation reaction occurs in an acidic environment. To ensure an acidic environment on the hair following the application of the oxidizer component, it is preferred that a composite composition obtained by the admixture of the hair dye lotion and the oxidizer component be acidic. Generally, this is accomplished by using a slightly basic (pH 7 to 8.5) hair dye lotion and an acidic (pH 2 to 6.5) oxidizer component. However, it is within the scope of this invention to maintain the hair dye lotion acidic and the oxidizer component slightly basic, or to have both compositions acidic. It is also suitable to provide an extraneous third composition having an acidic pH that is admixed with one of the hair dye lotion or the oxidizer component. It is of course understood that the aforementioned composite composition would not be applied to the hair of the consumer because the process of this invention is a two step process contemplating the sequential application of the hair dye lotion and the oxidizer component.

Melanin precursors which may be employed in the practice of this invention include DHIN and its derivatives (including analogs and homologs) and other melanin forming compounds represented by the formula:

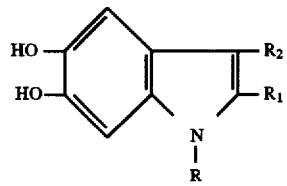

(I)

wherein R represents hydrogen, alkyl, hydroxyalkyl, aminoalkyl, aryl and substituted aryl containing up to three reaction inert substituents such as OH, $NH_2$, $NO_2$, alkyl, and alkoxy, the alkyl group of such reaction inert substituent containing up to two carbon atoms, and the alkyl group of the R substituent having up to six carbon atoms; $R_1$ and $R_2$, which may be the same or different, represent hydrogen and alkyl containing up to six carbon atoms or, when $R_2$ is H, $R_1$ may be $COOR_3$, in which $R_3$ may be H or a $C_1$ to $C_6$ alkyl, and mixtures of said compounds. Under the acidic conditions used herein, DHIN is useful because it is oxidized to dopaminochrome which rearranges to DHI. The DHI then converts to melanin in accordance with the invention. Any derivative, analog or homolog of DHIN that forms a compound of structure I above can be used in accordance with the present invention.

The preferred N-substituted compounds of the present invention are those of structure I where R is hydrogen, alkyl, hydroxyalkyl, and aminoalkyl, the alkyl group containing 1 to 2 carbon atoms. $R_1$ is preferably H and COOH, with $R_2$ preferably H. The most preferred compounds are DHI and DHIN.

For convenience, the invention will hereinafter be described principally with reference to DHI, but it should be remembered that the invention is applicable to all of the compounds defined herein as well as their equivalents. The various compounds may be used alone or in numerous mixtures, including mixtures with other oxidative dyes or with DHICA or its lower alkyl esters, to achieve a variety of shades and tonal qualities with hair fibers.

The concentration of the melanin dye precursor in the hair dye lotion is generally from about 0.05 to 10%, preferably from about 0.1 to 5%, especially from 0.1 to 2.5%. DHI, as is known, is rather unstable and subject to air oxidation. It is therefore usually provided under conditions that substantially exclude air, and made, for example, in accordance with the teachings of U. S. Pat. No. 5,492,541, incorporated herein by reference. All percents by weight defined in this disclosure and claims are percents by weight based on the total weight of the composition.

The iodate salts appear to be unique for this application. The same results are not achieved when other halogenate salts are employed as substitutes for the iodates. Surprisingly, the results obtained with a periodate salt in concert with hydrogen peroxide are also inferior to the results obtained with the iodate salts of the present invention.

Suitable iodate salts are the alkali metal, ammonium and alkaline earth iodate salts. The useful salts are sufficiently soluble in the media in which they are provided to provide a concentration as set forth below, and are also sufficiently soluble as used to effect, along with the peroxide component, the requisite oxidation of the melanin precursor as herein described. The preferred iodate salts are ammonium iodate, sodium iodate and potassium iodate. Sodium iodate is especially preferred. The iodate component may be contained in the same composition as the peroxide component, or may be provided in a separate container for admixture with the peroxide component just prior to use, or for separate application to the hair of the consumer following the application of the hair dye lotion. When applied separately, the iodate may be applied to the hair before, with or after application of the peroxide. It is preferred to apply the iodate and peroxide as a single composition. The iodate in the oxidizer component is present in an amount effective, in association with the peroxide component, to convert the melanin precursor to melanin within the time period set forth herein. Typically, the iodate concentration is from about 0.1 to about 10%, preferably from about 1 to about 8%, by total weight of the oxidizer component.

The peroxide component is most preferably hydrogen peroxide, although other peroxides such as solid adducts of hydrogen peroxide, e.g., urea peroxide, are known for oxidatively dyeing hair. A peroxide source such as percarbonate or perborate might also be useful in the practice of this invention. The peroxide is present in the oxidizer component in an amount effective, in association with the iodate component, to convert the melanin precursor to melanin within the time period set forth herein. Typically, the peroxide concentration is from about 0.5 to about 10%, preferably from about 2 to about 8%, by total weight of the oxidizer component. Generally, the weight ratio of peroxide to iodate salt in the oxidizer component is above about 2:1, and typically between 5:1 to 25:1.

It has been observed that a pretreatment of the hair with a reducing agent is often useful to enhance the formation of color with the selected melanin precursor. This treatment appears to make hair more porous and permits better penetration of the melanin precursor so that more melanin is produced in the hair than on it. Alternately, the reducing agent may be incorporated in the hair dye lotion(s). The effectiveness of a specific reducing agent varies with concentration. Useful reducing agents include, for example, sulfites, bisulfites and thioglycolic acid.

Sodium sulfite gives useful results at a concentration of from about 1 to 10%. Thioglycolic acid may be employed at from about 1 to 2%. At higher concentrations it appears to inhibit melanin formation and provides only lighter browner tones on subsequent treatment with the iodate / hydrogen peroxide oxidizer component in accordance with the invention. Ammonium bisulfite at a concentration of about 0.1 to 5%, preferably 1 to 2%, is the preferred reducing agent.

Nonmelaninic primary intermediates and couplers (hereinafter sometimes called "reactants") used in the practice of the process of the present invention are provided in amounts that are about the same as utilized in conventional oxidative hair dye processes. The tinctorially effective amount varies with the selected reactants, as is well known in the art. The skilled artisan will have no difficulty in selecting the reactants and the amounts to be employed. Generally, each reactant will be present in an amount of from about 0.01 to 5%, preferably 0.1 to 2%. Any of the conventional oxidizable primary intermediates and coupling agents can be employed in the compositions of this invention to achieve, together with the DHI, a wide variety of tints and hues.

Table 1 below lists some of the preferred primary intermediates and couplers for use in this invention.

TABLE 1

PRIMARY INTERMEDIATES:

3-methyl-4-aminophenol
2-hydroxyethyl-p-phenylenediamine
p-phenylenediamine
p-aminophenol
o-aminophenol
N,N-bis(2-hydroxyethyl)p-phenylenediamine
2,5-diaminopyridine
p-toluenediamme

COUPLERS:

resorcinol
o-aminophenol
1-naphthol
5-amino-o-cresol
2-methylresorcinol
2-methyl-1-naphthol
2,4-diaminophenoxy ethanol
4,6-di(hydroxyethoxy)-m-phenylenediamine
m-phenylenediamine
m-aminophenol Well known conventional additives usually employed in oxidative hair coloring compositions such as thickeners, surface active agents, antioxidants and fragrances may be included in the several compositions of the invention. Such compositions are preferably liquid solutions, but they may be in the form of emulsions, suspensions, lotions, or gels.

Surface active agents employed in the dyeing compositions of this invention can be amphoteric, anionic, nonionic or cationic. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chloride salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glyceryl monostearate; triethanolamine oleate; sodium salt of palmitic methyl taurine; cetyl pyridinium chloride; lauryl sulfonate; myristyl sulfonate; lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; 2-amino-2-methyl propanol; triethanolamine salt of p-dodecylbenzene sulfonate; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isethionate; sodium dodecyl sulfate and the sodium salt of 3-diethyl tridecanol-6-sulfate and the like. The quantity of surface active agent can vary over a wide range, typically from about 0.05 to 15%, preferably from about 0.01 to 5% by weight of the composition.

A thickening agent may also be incorporated in the dyeing composition of this invention which may be one or several of those commonly used in hair dyeing. These are exemplified by such products as sodium alginate or gum arabic, or cellulose derivatives, such as methylcellulose e.g., Methocel 60 HG, or the sodium salt of carboxymethylcellulose, or hydroxyethylcellulose, e,g,, Cellosize QP40 or acrylic polymers, such as polyacrylic acid sodium salt, or inorganic thickeners, such as bentonite. The quantity of this thickening agent can also vary over a wide range, even as high as 20%. Ordinarily it will range from about 0.5 to 5% by weight of the composition. The viscosity of the composition may vary from about 1 cps to about 100,000 cps. Especially from about 250 cps to about 10,000 cps, which viscosity is generally sufficient to avoid appreciable "running" of the composition on the face of the consumer.

The hair dye lotion and the oxidizer component compositions of this invention as applied to the hair are preferably aqueous compositions. The term aqueous composition is used herein in its usual generic sense as embracing any water-containing composition useful for the present purposes. This includes true solutions of the dye components aqueous medium, either alone or in conjunction with other materials, which are also dissolved or dispersed in the aqueous medium. The term aqueous composition also encompasses any mixture of the iodate/hydrogen peroxide and dye precursor with the aqueous medium either alone or together with other ingredients. The various components may be colloidally dispersed in the medium or may merely be intimately mixed therein. Moreover, the aqueous medium may comprise water or water and an auxiliary solvent. Typical auxiliary solvents which may be used to enhance the solubility of the components include ethanol, carbitol, isopropanol, propylene glycol, ethylene glycol, diethyleneglycol, diethylene glycol monoethylether, glycerin, etc.

The compounds employed in this invention are all known or can be prepared by known procedures.

Typically, equal volumes of the hair dye lotion and the oxidizer component are employed, although this is not critical as long as the amount of liquid composition is sufficient to work into the hair. For example, one package may contain the hair colorant with or without oxidation dye precursors. A second package may contain the hydrogen peroxide at a pH of about 3 to 4. Any conventional organic or inorganic acid may be employed to achieve the desired pH. The compositions may be stabilized, for example with a stannate salt. Dye lotion to oxidizer component volume ratios of from 1:3 to 3:1 are suitable for the practice of this invention.

The selected iodate may be in the form of the dry salt or in an aqueous composition which may be acidic and contain thickeners or surfactants such as those described above.

The term "package" is used in the widest possible sense. It includes packages such as might be sold to an individual consumer with all of the packages in the same container. It includes also separate compositions in large amounts, such as might be sold to a beauty salon, whether or not the separate compositions are sold in the same container.

The compositions may be applied to the hair employing any of the usual procedures. One convenient method is to apply the hair dye lotion in alkaline solution and, after a sufficient time for penetration, e.g. 5 to 30 minutes, especially 10 to 20 minutes, to apply the iodate and peroxide composition(s) for 1 to 30 minutes, preferably 5 to 15 minutes, in acid solution.

The applicability of hair coloring of the compositions of this invention is evaluated by determination of tristimulus values. The tristimulus values are standard Hunter chromaticity values obtained by procedures well known to those skilled in the art. The values manifest the ability of the compositions of the invention to be usefully employed in hair coloring processes. In the Hunter Tristimulus System, L is a measure of lightness and darkness that is, the depth of the color of the hair tress. The lower the value of L the darker the color. A decrease in the value of L indicates a darkening of the hair tress. In the case of bleached and blended gray hair, a lowering of the value of L shows deposition of hair dye on the tress. The a value is a measure of the greenness or redness of the hair's color. As the a value increases, the hair has a more prominent red tonality. A lowering in the a value results in greener shades. The b value is a measure of the yellow and blue color. Higher b values indicate a more yellow hue in the hair.

The following examples are illustrative of the invention.

EXAMPLE 1

A swatch of gray hair (Hunter values L 34.6 a 0.1 b 7.7) was placed in an aqueous solution, containing 5,6-dihydroxyindole (0.5%) and sodium bisulfite (0.2%). The pH of the solution was adjusted to approximately 7.5 with bicarbonate/citric acid. The hair was left in contact with the solution for 20 minutes. Afterwards the hair was rinsed with water. The swatch was placed in an aqueous solution of $NH_4IO_3$ (1%) and $H_2O_2$ (3%) for 5 minutes. This solution had been prepared by mixing a commercial 6% $H_2O_2$ solution (Clairoxide, 20 Volume) with a 2% aqueous solution of $NH_4IO_3$ one to one (by weight). Finally, the hair was rinsed, shampooed and dried. The swatch was dyed to a dark-brown to black color (Hunter values L 15.2 a 0.7 b 0.9).

EXAMPLE 2

A swatch of commercially bleached hair (Hunter values L 64.7 a 1.4 b 18.50) was treated as described in Example 1. The hair was dyed to a dark brown to black color (Hunter values L 13.8 a 0.6 b 1.2).

EXAMPLE 3

The dyed hair swatch of Example 1 was placed in a 12% solution of a commercial shampoo and shaken for 1 hour. Afterwards, the hair was rinsed and dried. There was no noticeable change in the color of the hair as a result of shampooing (Hunter values L 15.0 a 0.8 b 1.8). This example demonstrates the wearing properties of hair dyed according to the invention.

EXAMPLE 4

The dyed hair swatch of Example 2 was placed in a fade-o-meter and exposed to light for 72 hours at 50° C. After this treatment, there was only a small change of the hair color (Hunter values L 15.4 a 1.1 b 2.8). This is a further demonstration of the wearing properties of hair dyes using the compositions of the invention.

EXAMPLE 5

Piedmont hair (Hunter values L 66.6 a 0.8 b 21.8) was soaked in an aqueous solution of 1% DHI; 0.1% $Na_2SO_3$ for 30 minutes. The hair was rinsed with water. Afterwards the hair was exposed to a solution, containing 2% $NaIO_3$ and 6% $H_2O_2$ for 5 minutes. The hair was dyed to a dark gray color (Hunter values L 17.1 a 0.9 b 1.1). When Piedmont hair with the same Hunter values was similarly treated except that 0.5% $NH_4IO_3$ was used, instead of 2% $NaIO_3$, the hair was dyed black (Hunter values L12.9 a 0.4 b 0.2). This shows that ammonium iodate is significantly more effective than sodium iodate.

EXAMPLE 6

This example demonstrates that iodate salts are far more efficient in color development than bromate or chlorate salts. In each instance the hair employed was from the same lot of commercially bleached hair (Hunter values L61.3 a 4.0 b 22.2).

A hair swatch was treated with an aqueous solution of DHI (0.5%) and sodium sulfite (0.2%) for 20 minutes. The hair was rinsed with water. Afterwards, the hair was exposed to an aqueous solution, containing 3% $H_2O_2$ and 5% $NaIO_3$. The hair was dyed black (Hunter values L 12.0 a 0.3 b 0.1).

A hair swatch was similarly treated except that 5% $NaBrO_3$ was used instead of 5% $NaIO_3$. The hair was dyed to a gray color (Hunter values L 19.2 a 0.4 b 1.0).

A third hair swatch was treated in the same manner with the exception, that 5% $NaClO_3$ was used instead of 5% $NaIO_3$. The hair was dyed to a gray color (Hunter values L 19.2 a 0.4 b 1.0).

EXAMPLE 7

This example illustrates the use of the novel dye compositions of the invention together with standard oxidation dyes.

A swatch of gray hair (Hunter values L 34.6 a 0.1 b 7.7) was exposed to a solution of 0.5% DHI; 0.5% 5-amino-o-cresol and 0.1% sodium sulfite for 20 minutes before being rinsed with water. Afterwards, the hair was exposed to a solution of 3% $H_2O_2$ and 1% $NH_4IO_3$ for 5 minutes. The hair was then rinsed, shampooed and dried. The color of the hair was brown (Hunter values L 17.0 a 2.5 b 4.2).

A swatch of bleached hair (Hunter values L 64.7 a 1.4 b 18.5) was exposed to a solution of 0.5% DHI; 0.5% 5-amino-cresol, 0.5% p-aminophenol and 0.1% sodium sulfite for 20 minutes before being rinsed with water. Afterwards, the hair was exposed to a solution of 3% $H_2O_2$ and 1% $NH_4IO_3$ for 5 minutes. The hair was then rinsed, shampooed and dried. The color of the hair was brown (Hunter values L 14.5 a 2.1 b 2.9).

EXAMPLE 8

A swatch of gray hair (Hunter values L 34.6 a 0.1 b 7.7) was placed in an aqueous solution containing 5,6-dihydroxyindole (0.5%). The pH of the solution was adjusted to approximately 7.5 with bicarbonate/citric acid. The hair was left in contact with the solution for 20 minutes. Afterwards the hair was rinsed with water. The swatch was placed in an aqueous solution of $NH_4IO_3$ (1%) and $H_2O_2$ (3%) for 5 minutes. This solution had been prepared by mixing a commercial 6% $H_2O_2$ solution (Clairoxide, 20 Volume) with a 2% aqueous solution of $NH_4IO_3$ one to one (by weight). Finally, the hair was rinsed, shampooed and dried. The swatch was dyed to a dark-brown to black color (Hunter values L 16.0 a 0.8 b 1.0).

What is claimed is:

1. A process for dyeing hair comprising (a) applying to the hair an aqueous hair dye lotion containing a melanin precursor in an amount effective to dye hair, and (b) thereafter applying to the hair an effective oxidizing amount of an oxidizer component comprising a hydrogen peroxide oxidizing agent together with a water soluble ammonium, alkali metal or alkaline earth metal iodate, at least one of the hair dye lotion or the oxidizer component being sufficiently acidic such that the oxidation of the melanin precursor on the hair following step (b) takes place at an acidic pH.

2. The process of claim 1 wherein the melanin precursor is present in the hair dye lotion in an amount of from about 0.05 to about 10% by weight of the hair dye lotion, and wherein the hair dye lotion has a basic pH.

3. The process of claim 1 wherein by total weight of the oxidizer component the peroxide is present in an amount of from about 0.5 to about 10% and the iodate is present in an amount of from 0.1 to 10%, said oxidizer component having an acidic pH.

4. The process of claim 3 wherein the oxidizer component is applied to the hair in two stages, the first stage being the application of an iodate-containing composition and the second stage being the application of a peroxide-containing composition, either the first or second stage being applied to the hair following application of the hair dye lotion to the hair.

5. The process of claim 3 wherein the oxidizer component is a single composition.

6. The process of claim 1 wherein the melanin precursor is selected from the group consisting of 5,6-dihydroxyindoline and its derivatives, a dihydroxyindole, and mixtures thereof, the dihydroxyindole being represented by the formula:

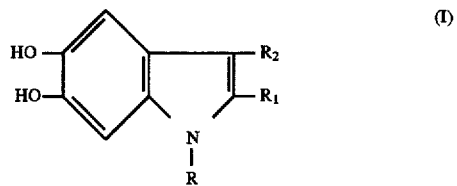

(I)

where R is hydrogen, alkyl, hydroxyalkyl, aminoalkyl, aryl, or substituted aryl containing up to three reaction inert substituents, the alkyl group containing up to six carbon atoms; $R_1$ and $R_2$, which may be the same or different, represent hydrogen or alkyl containing up to six carbon atoms, or, when $R_2$ is H, $R_1$ may represent $COOR_3$, wherein $R_3$ is H or alkyl having up to six carbons.

7. The process of claim 6 wherein the melanin precursor is 5,6-dihydroxyindole.

8. The process of claim 4 in which an amount of an oxidative primary intermediate and coupler sufficient to reactively form a tinctorially effective amount of hair dye is contained in at least one of the hair dye lotion, the peroxide-containing composition, or the iodate-containing composition.

9. The process of claim 5 in which an amount of an oxidative primary intermediate and coupler sufficient to reactively form a tinctorially effective amount of a hair dye is contained in at least one of the hair dye lotion, the oxidizer component, or is contained in an aqueous second hair dye lotion.

10. The process of claim 1 wherein the hair is treated with an aqueous solution of a reducing agent in advance of or simultaneously with the application of the hair dye lotion.

11. The process of claim 10 wherein said reducing agent is thioglycolic acid or a sulfite or bisulfite salt and wherein the reducing agent concentration in the aqueous solution is from 1 to 2% when the reducing agent is thioglycolic acid, and 1–10% when the reducing agent is a sulfite or bisulfite salt.

12. A process for dyeing human hair comprising (a) contacting the hair to be dyed with an aqueous hair dye lotion comprising 0.05 to 10% by weight of a melanin precursor selected from the group consisting of 5,6-dihydroxyindoline and its derivatives, a dihydroxyindole and mixtures thereof, the dihydroxyindole being represented by the formula:

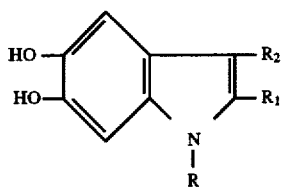

(I)

wherein R is hydrogen, alkyl, hydroalkyl, aminoalkyl, aryl, or substituted aryl containing up to three reaction inert substituents, the alkyl group containing up to six carbon atoms; $R_1$ and $R_2$, which may be the same or different, represent hydrogen or alkyl containing up to six carbon atoms or, when $R_2$ is H, $R_1$ may represent $COOR_3$, wherein $R_3$ is H or alkyl of up to six carbons, and (b) thereafter contacting the hair with an aqueous oxidizer component containing from about 0.5 to 10% of a hydrogen peroxide oxidizing agent together with from about 0.1 to 10% of an iodate selected from the group consisting of alkali and alkaline earth metal iodates and ammonium iodate, said oxidizer component being a single composition containing the peroxide and the iodate, or separate aqueous compositions containing, respectively, the peroxide and iodate, the separate compositions being sequentially applied to the hair to be dyed following step (a), at least one of the oxidizer component, whether a single composition or two separate compositions, or the hair dye lotion being sufficiently acidic such that the oxidation of the melanin precursor on the hair following step (b) takes place at an acidic pH.

13. The process of claim 12 in which an amount of an oxidative primary intermediate and coupler sufficient to reactively form a tinctorially effective amount of hair dye is contained in at least one of the hair dye lotion, the single composition oxidizer component, the iodate composition, or the peroxide composition.

14. The process of claim 12 wherein R is H, methyl, ethyl or hydroxyethyl; $R_1$ is H or COOH, and $R_2$ is H.

15. The process of claim 12 wherein the melanin precursor is 5,6-dihydroxyindole.

16. A kit for dyeing hair comprising (a) a first container containing a hair dye lotion containing 0.05 to 10% of a melanin precursor selected from the group consisting of 5,6-dihydroxyindoline and its derivatives, a dihydroxyindole and mixtures thereof, the dihydroxyindole being represented by the formula:

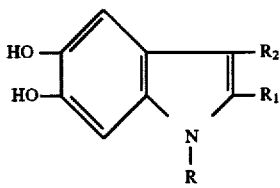

(I)

wherein R is hydrogen, alkyl, hydroalkyl, aminoalkyl, aryl, or substituted aryl containing up to three reaction inert substituents, the alkyl group containing up to six carbon atoms; $R_1$ and $R_2$, which may be the same or different, represent hydrogen or alkyl containing up to six carbon atoms or, when $R_2$ is H, $R_1$ may represent $COOR_3$, wherein $R_3$ is H or alkyl of up to six carbons; (b) a second container, (c) an optional third container, and (d) written instructions for dyeing hair in accordance with claim 1, the second container containing an aqueous composition of a peroxide oxidizing agent and optionally an iodate selected from the group consisting of alkali and alkaline earth metal iodates and ammonium iodate, the optional container containing said iodate when the iodate is not contained in the second container.

* * * * *